(12) United States Patent
Top et al.

(10) Patent No.: US 12,097,017 B2
(45) Date of Patent: Sep. 24, 2024

(54) METHOD FOR ELECTRONIC CALIBRATION OF MAGNETIC PARTICLE IMAGING SYSTEM

(71) Applicant: ASELSAN ELEKTRONIK SANAYI VE TICARET ANONIM SIRKETI, Ankara (TR)

(72) Inventors: Can Baris Top, Ankara (TR); Alper Gungor, Ankara (TR); Serhat Ilbey, Ankara (TR); Huseyin Emre Guven, Ankara (TR)

(73) Assignee: ASELSAN ELEKTRONIK SANAYI VE TICARET ANONIM SIRKETI, Ankara (TR)

( * ) Notice: Subject to any disclaimer, the term of this patent is extended or adjusted under 35 U.S.C. 154(b) by 388 days.

(21) Appl. No.: 17/311,705

(22) PCT Filed: Dec. 11, 2018

(86) PCT No.: PCT/TR2018/050791
§ 371 (c)(1),
(2) Date: Jun. 8, 2021

(87) PCT Pub. No.: WO2020/122823
PCT Pub. Date: Jun. 18, 2020

(65) Prior Publication Data
US 2022/0022769 A1   Jan. 27, 2022

(51) Int. Cl.
*A61B 5/0515*   (2021.01)
*G01R 33/00*   (2006.01)
(Continued)

(52) U.S. Cl.
CPC ........ *A61B 5/0515* (2013.01); *G01R 33/0023* (2013.01); *G01R 33/1276* (2013.01); *G01R 35/005* (2013.01)

(58) Field of Classification Search
None
See application file for complete search history.

(56) References Cited

U.S. PATENT DOCUMENTS

2009/0115415 A1*   5/2009   Weaver .................... A61B 5/05
                                             324/309
2011/0273176 A1*  11/2011   Weaver .................... A61B 5/05
                                             977/773
(Continued)

OTHER PUBLICATIONS

Serhat et.al.; Coded Scenes for Fast System Calibration in Magnetic Particle Imaging; 2018 IEEE 15th International Symposium on Biomedical Imaging ISBI 2018) Apr. 4-7, 2018, Washington, 0.C., USA (Year: 2018).*

*Primary Examiner* — Nasima Monsur
(74) *Attorney, Agent, or Firm* — Bayramoglu Law Offices LLC

(57) ABSTRACT

A method for electronic calibration of a magnetic particle imaging system is provided by proposing a coded calibration scene that contains multiple nanoparticle samples distributed randomly or pseudo-randomly inside a volume of the coded calibration scene where nanoparticle positions are changed virtually multiple times to create different calibration scenes. Virtual effect is created with current carrying electromagnets surrounding the nanoparticle samples. The method comprises: placing a plurality of nanoparticle samples inside a calibration scene; surrounding the plurality of nanoparticle samples with one or more electromagnets; applying a current to the one or more electromagnets to cause a magnetic field offset at a desired amplitude to virtually move the plurality of nanoparticle samples to a desired position; generating a system matrix with compressed sensing methods by using measurements taken for different current excitations of the one or more electromag- (Continued)

nets, wherein the plurality of nanoparticles samples are virtually in different positions.

11 Claims, 6 Drawing Sheets

(51) Int. Cl.
   *G01R 33/12* (2006.01)
   *G01R 35/00* (2006.01)

(56) References Cited

U.S. PATENT DOCUMENTS

| | | | |
|---|---|---|---|
| 2012/0126800 A1* | 5/2012 | Vernickel | A61B 5/0515 324/234 |
| 2015/0097576 A1* | 4/2015 | Berman | G01R 33/09 324/601 |
| 2015/0221103 A1* | 8/2015 | Knopp | G06T 11/005 324/300 |
| 2017/0020407 A1* | 1/2017 | Weber | A61B 5/7257 |
| 2017/0067972 A1* | 3/2017 | Diamond | G01R 33/1276 |

* cited by examiner

Reference (N=80×40=3200)
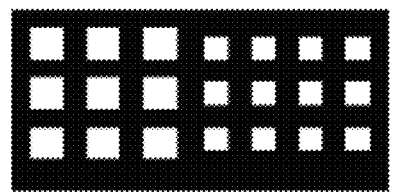
Standard Compressed Detection
M=2560      M=1600      M=640
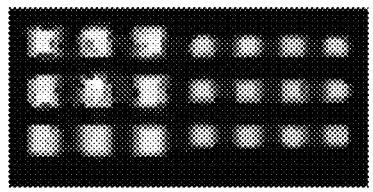 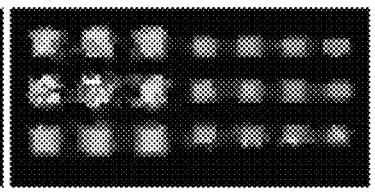 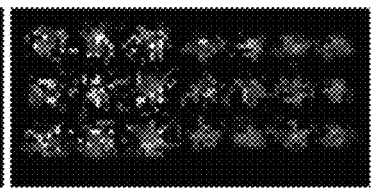
Proposed Method
M=320      M=160      M=97
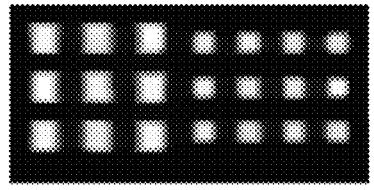 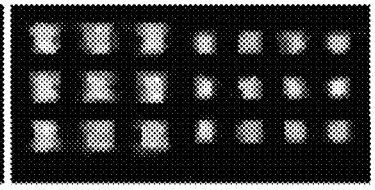 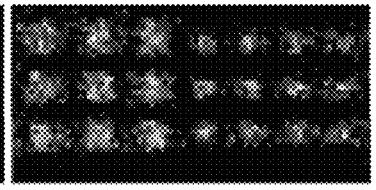
FIG. 4
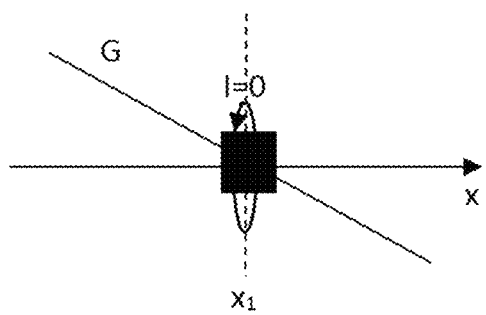 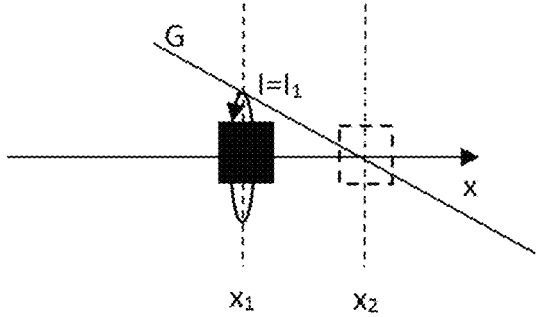
FIG. 5          FIG. 6

METHOD FOR ELECTRONIC CALIBRATION OF MAGNETIC PARTICLE IMAGING SYSTEM

CROSS REFERENCE TO THE RELATED APPLICATIONS

This application is the national stage entry of International Application No. PCT/TR2018/050791, filed on Dec. 11, 2018, the entire contents of which are incorporated herein by reference.

TECHNICAL FIELD

The present disclosure relates a method for electronic calibration of magnetic particle imaging system by proposing a coded calibration scene that contains multiple nanoparticle samples distributed inside its volume where nanoparticle positions are changed virtually multiple times to create different calibration scenes.

BACKGROUND

Magnetic nanoparticles can be used for various purposes in medicine such as angiography, stem cell tracking, imaging of cancerous cells and targeted drugs. Magnetic nanoparticles can be imaged non-invasively using the Magnetic Particle Imaging (MPI) method. Two different methods are used as standard for image reconstruction in the magnetic particle imaging method.

The first one is the system calibration method as stated in U.S. Pat. No. 8,355,771B2 numbered patent, in which a small volume nanoparticle sample is scanned mechanically at the desired system resolution steps in the field of view to obtain the calibration data of the system [1]. Images are generated using this calibration data (which is also called the system matrix). In the standard system calibration method, the calibration measurements last very long since the sample nanoparticle must be mechanically scanned and measured at every grid point in the field of view. The mechanical scanning time from one point to the other and acquisition of the measurement data takes about 1.3 sec [2]. For a small field of view having 30×30×30 grid points, the calibration time lasts 9.75 hours. In clinical practice, the calibration of a larger imaging volume may last for months. There is a need to calibrate the system frequently, since nanoparticle characteristics are known to vary from batch to batch and is also affected by the imaging sequence. For this reason, standard system calibration method cannot be practically adopted for systems with large field of view. In addition, since the nanoparticle to be scanned must be smaller than the voxel size of the image, the number of nanoparticles in the scanned sample is limited and the signal-to-noise ratio is small. A method to increase the signal-to-noise ratio is multiple data acquisition at the same position, and averaging. Therefore, the mechanical motion cannot be continuous, and the scanner should be stopped at every grid point, and moved to the next point after taking enough measurements to reach to the desired signal noise level. This limits the speed of the calibration measurements.

Recently, a calibration method has been proposed in an application no. US20150221103A1, in which the nanoparticle sample is scanned at random positions much fewer than the total number of voxels in the field of view. This is possible according to the compressed sensing theory [3] since the system matrix is sparse in certain transform domains (discrete Fourier, cosine, or Chebychev). It has been shown that this method can reduce the number of scanned points by 80-90%. Instead of taking measurements from all of the voxels (N) in the field of view, system calibration can also be done by making reduced number of measurements at random M (<N) voxel positions using compressed sensing techniques. Since it is not possible to calculate how small M should be analytically, the M/N ratio should be chosen according to the image quality. Experimental images were obtained in the above mentioned reference. While image quality was acceptable for M/N=0.1, it was significantly degraded for lower M/N ratios. The calibration time can be reduced by a factor of 10 with this method but very long calibration times are still needed since the sample is mechanical scanned, i.e. a measurement area of 200×200×200 points will take longer than 10 days to measure.

The second reconstruction method is the X-space approach used in application numbered EP3143929A1. In this method, there is no calibration step; images are generated using the signal equation model for the magnetic particles imaging. Image reconstruction is done in the time domain by using the MPI signal equation. In this method, deviations from the ideal of MPI hardware are not taken into account and the resolution is lower than the system calibration method.

A von Gladiss et al. [2] discloses an electronic calibration method for accelerating calibration procedure. In this method, the nanoparticle sample is placed in a separate calibration unit, which can generate homogeneous magnetic fields of any orientation imitating the magnetic fields that the nanoparticle sample would be exposed in the MPI system. Although this method provides faster calibration than the standard method, it requires the use of a separate calibration unit; the magnetic field distribution of the MPI system must be separately measured in the field of view; and the calibration unit measurements must be related to the MPI system measurements. Since magnetic field distribution measurements of the MPI system require mechanical scanning at each voxel in the field of view, as in the case of standard system calibration measurements, the advantage of electronic calibration is limited.

SUMMARY

In the present invention, a large calibration apparatus, which will be referred as an electronic coded calibration scene, is proposed for the calibration of an MPI system. Electronic coded calibration scene includes nanoparticle samples at multiple positions. There are one or more electromagnets around the nanoparticle samples that create a magnetic field at the desired amplitude. By controlling the currents of the electromagnets, the magnetic field is adjusted so that the nanoparticles behave as if they are in a different position. Nanoparticle positions are changed virtually multiple times to create different calibration scenes. Measurements taken from different calibration stages are used to obtain a system calibration matrix using compressed sensing methods.

The advantages that distinguish this method from other available methods are listed below:

As the calibration scenes are electronically changed, calibration can be done much faster compared to mechanical scanning calibration methods, i.e. US patent applications numbered U.S. Pat. No. 8,355,771B2 and US2015/0221103A1 [1]. In previous calibration methods, the nanoparticle specimen is usually mechanically scanned, so calibration takes a long time. There is no need for mechanical scanning an MNP sample in the method of present invention. All the effects of nanoparticles, the MPI hardware, and magnetic field inhomogeneities are measured using a single calibration apparatus without the need for mechanical scan.

BRIEF DESCRIPTION OF THE DRAWINGS

FIG. 4 shows comparison of the standard compressed detection method with the proposed method for the same noise level using a simulation model. Proposed method shows better image quality with smaller number of measurements (M).

FIG. 5 shows a nanoparticle sample placed at position $x_1$ in a one-dimensional imaging system on the x-axis.

FIG. 6 shows virtual position of the nanoparticle sample in FIG. 5 under magnetic field.

PART REFERENCES

Figure 1:
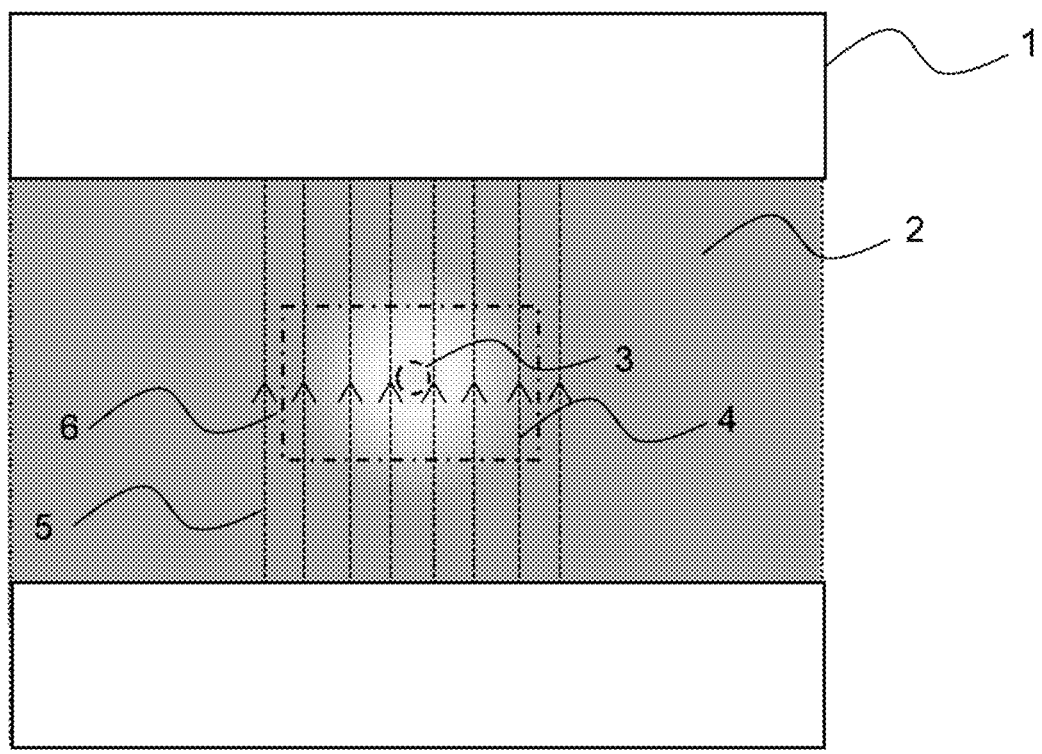
FIG. 1 shows the cross section of the bore of a magnetic particle imaging setup, the distribution of non-homogeneous primary magnetic field having two zones and homogeneous secondary magnetic field, and the field of view.
Figure 2:
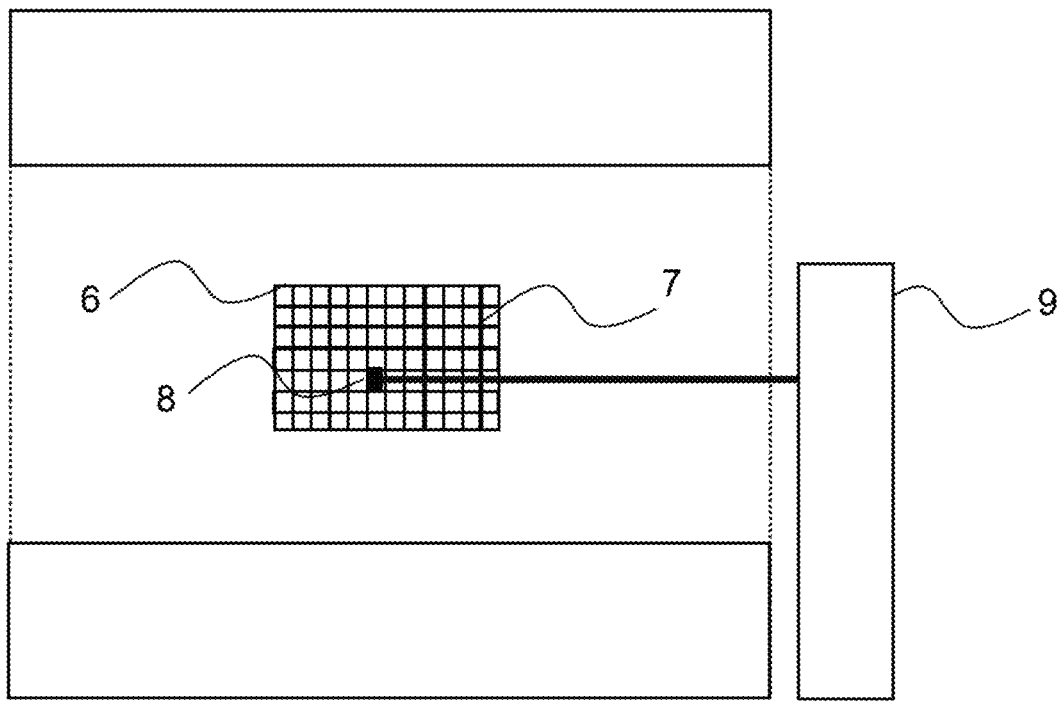
FIG. 2 shows an entire field of view that is hypothetically divided into small voxels and a calibration setup using a sample containing the nanoparticles.
Figure 3:
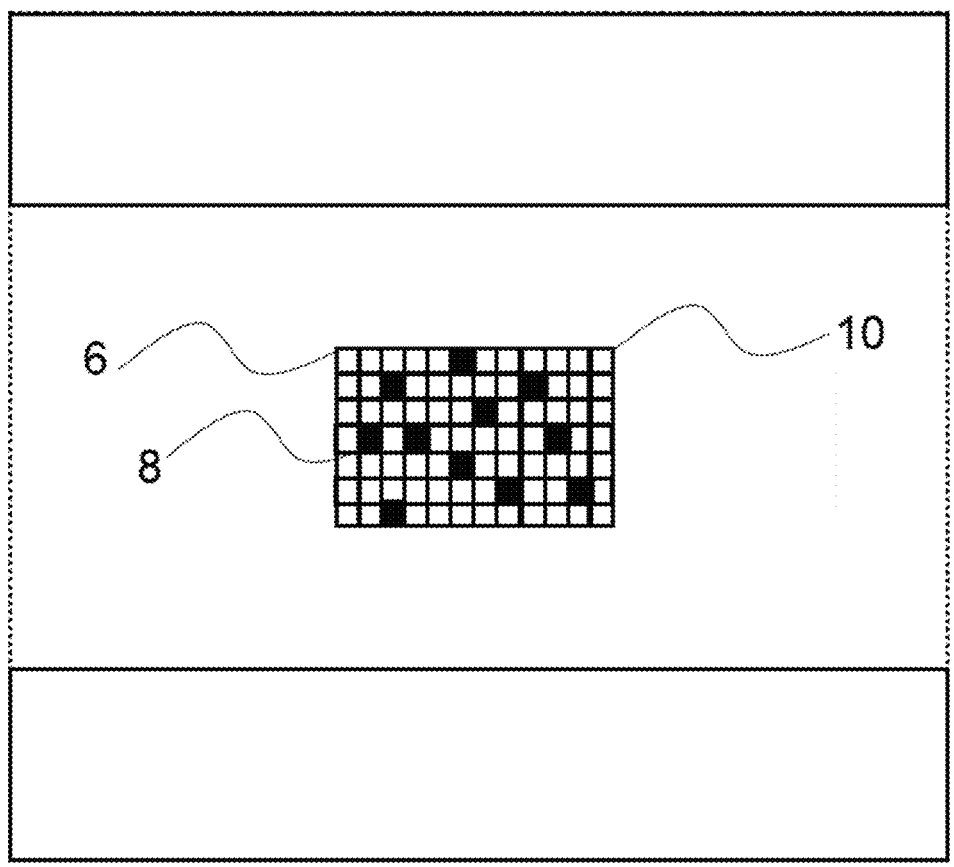
FIG. 3 shows a coded calibration scene with a plurality of nanoparticle samples distributed randomly or pseudo-randomly inside its volume.

1. MPI system
2. Primary magnetic field
3. First zone of the primary magnetic field
4. Second zone of the primary magnetic field
5. Secondary magnetic field
6. Field of view
7. Voxel
8. Magnetic nanoparticle sample
9. Mechanical scanner
10. Coded calibration scene
11. Electronic calibration scene
12. Nanoparticle sample in the electronic calibration scene
13. Group of coil feed lines
14. Calibration scene interface with the MPI system
15a, 15b, 15c. Coils for applying magnetic field in three axes to a nanoparticle sample
16. Feed line for coils around a nanoparticle sample
17. A group of coils that are excited with the same current
18. Helmholtz coil configuration
19. Receiver coil
20. Transmitter coil Detailed Description of the Embodiments In an MPI system (1) that consists of a magnetic field generator and a measurement device (FIG. 1), the distribution of magnetic nanoparticles is imaged using a non-homogeneous primary magnetic field (2) having two zones [4]. The first (3) of these two zones has a very low magnetic field intensity and is called the field free region (FFR). The magnetic nanoparticles in the FFR can be magnetized in the direction of a secondary external magnetic field (5). In the second zone (4), the magnetic field intensity is high and the magnetic nanoparticles in this region are in saturation. Therefore, they respond marginally to a secondary magnetic field (5). The secondary magnetic field (5) is applied to the entire field of view (6) as a time varying magnetic field. The time-dependent magnetization of the magnetic nanoparticles in the FFR is measured by the receiving coil(s). The amplitude of the measured signal is directly proportional to the number of nanoparticles in the FFR. The FFR is scanned electronically or mechanically throughout the field of view (6) to obtain the nanoparticle distribution in the field of view (6). Since the magnetic nanoparticles have a non-linear magnetization curve, the received signal from the particles in the FFR contains the harmonics of the frequency of the transmitted signal. The received signal properties depend on both the nanoparticle (size, shape, material, etc.) and solution properties (viscosity, temperature), and the magnetic field properties of the imaging system. In MPI, best image quality is achieved with the image reconstruction method based on the system calibration method, which takes all these effects into account [5].

In the system calibration image reconstruction method, firstly the entire field of view (6) is hypothetically divided into small voxels (7). A system matrix is formed using a sample (8) filled with a magnetic nanoparticle having a size of a voxel (7). To this end, the sample (8) containing the nanoparticles is scanned to every voxel position by means of a mechanical scanner (9). Secondary magnetic field signal is applied, and the nanoparticle signal received by the receiving coils is stored in a digital storage unit (e.g. hard disk). In practice, the measurement data are acquired multiple times at the same voxel point, and the signal to noise ratio is increased by averaging the measurements data. The measured signal from a single voxel is converted to the frequency domain using the Fourier transform, forming a column of the system matrix (A). The whole system matrix is generated by taking measurements at all voxel positions. This process is called the calibration step.

For imaging, measurement data are acquired by scanning the FFR inside the object, and the image is reconstructed using this measurement data and the system matrix. To this end, a linear equation set Ax=b is solved. In this equation set, A is the system matrix, b is the vector of measurements taken from the object, and x is the nanoparticle distribution inside the object. The major disadvantage of the system matrix calibration method is its long duration (about 1.3 seconds per voxel, multiplied by the number of voxels) [2]. In addition, since the sample size of the nanoparticle is very small, the signal level is low and it is necessary to increase the signal-to-noise ratio by taking multiple measurements. This prevents continuous mechanical scanning, leading to the prolongation of the measurement period.

The present invention proposes the use of coded calibration scenes (10) to solve the problems of the prior art. A coded calibration scene can be defined as an apparatus containing a plural number of nanoparticle samples, which are distributed randomly or pseudo-randomly inside its volume. This method has the advantages that the signal level increases proportional to the number of particles used in the calibration, and the condition of the compressed sensing problem is increased [6]. As a result, calibration is possible with fewer number of measurements using compressed sensing algorithms such as greedy reconstruction algorithms, approximate message passing, optimization based techniques, etc. [3].

According to the compressed sensing theory, the correlation of calibration scenes with each other should be minimized. For this reason, in a preferred embodiment, nanoparticles are distributed randomly or pseudo-randomly in each calibration scene.

An implementation of this method is as follows: the number of calibration scenes, M, to be measured is predetermined. For this, the simulation model of the imaging system can be used, or a number of calibration scenes are produced during the system tests of the produced imaging system; new scenes are measured until the image quality reaches a sufficient level from the medical point of view. The measurement data are collected and recorded for M coded calibration scenes. Once these measurements have been taken, the system matrix, A, is reconstructed using the following optimization problem:

$$\underset{A}{\mathrm{argmin}}\ \|DA^T\|_1 \text{ subject to } \|(PD^T)DA^T - A_p\|_2 < \varepsilon_p$$

where P is the nanoparticle density matrix for the measured coded calibration scenes, D is the transformation matrix that transforms the system matrix into a sparse domain, $A_p$ is the measurement matrix converted to Fourier space for each measurement position, $\varepsilon_p$ represents a constant related to the error caused by the system noise. Different algorithms in the literature can be used to solve abovementioned inequality (e.g. Fast Iterative Shrinkage Thresholding Algorithm (FISTA), Alternating Direction Method of Multipliers (ADMM) [7]).

This method is compared with the standard compressed detection method for the same noise level using a simulation model as revealed in FIG. 4. An object with N=3200 pixels was imaged both by using the standard compressed sensing calibration method with M=2560 calibration points and M=320 coded calibration scenes. The resultant image quality was poor for the standard compressed sensing method, while a high quality image was obtained with the coded calibration scenes.

In a preferred embodiment, points expressed by P can be selected from a domain that can be quickly transformed, such as the Hadamard matrix, in order to shorten the solution time of the problem given in the inequality. In this case, the P matrix can be expressed as a masked unitary transformation. It has previously been shown that the optimization problem can be solved efficiently in situations involving a masked unitary transformed space [8]. By this way, the problem of solution time can be further decreased.

In practice, the time for switching between the coded calibration scenes would be much longer than measurement time of a single coded calibration scene. Therefore, the total calibration duration would be determined by the total number of coded calibration scenes used and the time required for changing (replacement) of the coded calibration scenes. In the present invention, a single electronic coded calibration scene (11) is used, in which the nanoparticle positions are changed virtually by electronical means. For nanoparticle position control, one or more coils (15a, 15b, 15c) are located around the nanoparticle samples (12) in the electronic calibration scene (11). When current is applied to the coil(s) (15a, 15b, 15c), an offset is added to the magnetic field in the coil axis. This magnetic field offset results in virtual movement of the nanoparticle sample (12).

In an example as illustrated in FIG. 5, a nanoparticle sample is placed at position $x_1$ in a one-dimensional imaging system on the x-axis. The magnetic field $B_p(t)$ on this sample can be written as the sum of a primary magnetic field having gradient G in the x-direction and a secondary magnetic field in the x-direction sinusoidally changing in time with amplitude D and frequency $\omega$:

$$B_p(t) = G \cdot x_1 + D\sin(\omega t)$$

If there is a coil around the nanoparticle sample (12) generating a magnetic field with a magnitude $B_{xcal}$ in the x-direction, the magnetic field on the magnetic nanoparticle becomes:

$$B_p = G \cdot x_1 + D\sin(\omega t) + B_{xcal}$$

Since the nominal position of the magnetic nanoparticle sample (12) is determined by the direct current (DC) portion of $B_p(t)$, and the gradient of the primary magnetic field is unchanged, the new position $x_2$ detected by the system of the magnetic nanoparticle sample (12) can be calculated using the following equation:

$$G \cdot x_1 + B_{xcal} = G \cdot x_2$$

In this case, the virtual position of the nanoparticle sample is given in FIG. 6 and equals to:

$$x_2 = x_1 + \frac{B_{xcal}}{G}$$

By changing the current amplitude of the coil around the magnetic nanoparticle, the value of $B_{xcal}$ can be controlled. Thus, a plurality of calibration scenes can be obtained using a single calibration scene. It is possible to change the position of the nanoparticle sample in three axes by placing coils in the two other remaining axes.

Figure 7:
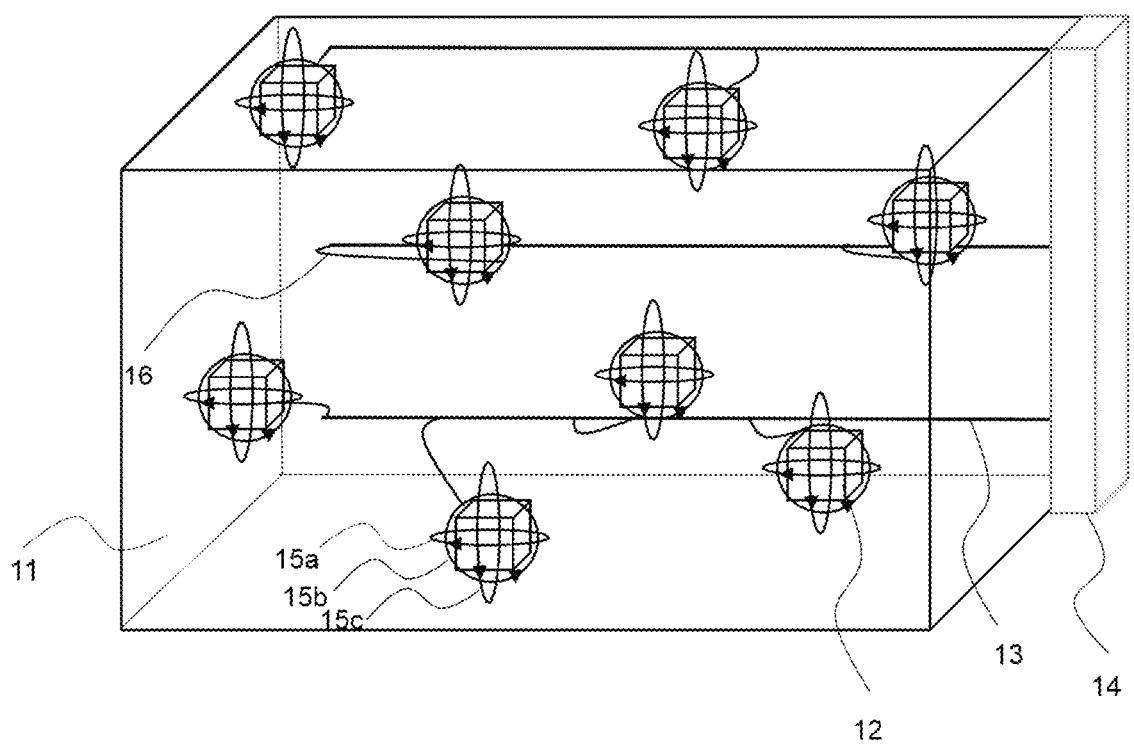
FIG. 7 shows an electronic calibration scene with 8 virtually displaceable nanoparticle samples.

An alternative embodiment of an electronic coded calibration scene (11) is shown in FIG. 7, comprising 8 virtually displaceable nanoparticle samples (12). The coils (15a, 15b, 15c) located around the nanoparticle samples (12) can be connected to the MPI system for calibration mode by means of an interface (14) terminating in the coil feed lines (13). The MPI system carries the currents required for the desired calibration scene positions in the calibration mode via this interface (14). After the measurement of each calibration scene, the currents required for the next calibration scene are adjusted by the MPI system and the measurements are repeated. The number of repetitions should allow the system matrix to be obtained correctly.

The nanoparticles in a voxel of the calibration stage must not be affected by the magnetic field of the coils in other voxels. For this reason, the nanoparticle samples should be separated. In the preferred implementation of calibration scene, the number of nanoparticle samples is less than 20% of the total number of voxels.

Figure 8:
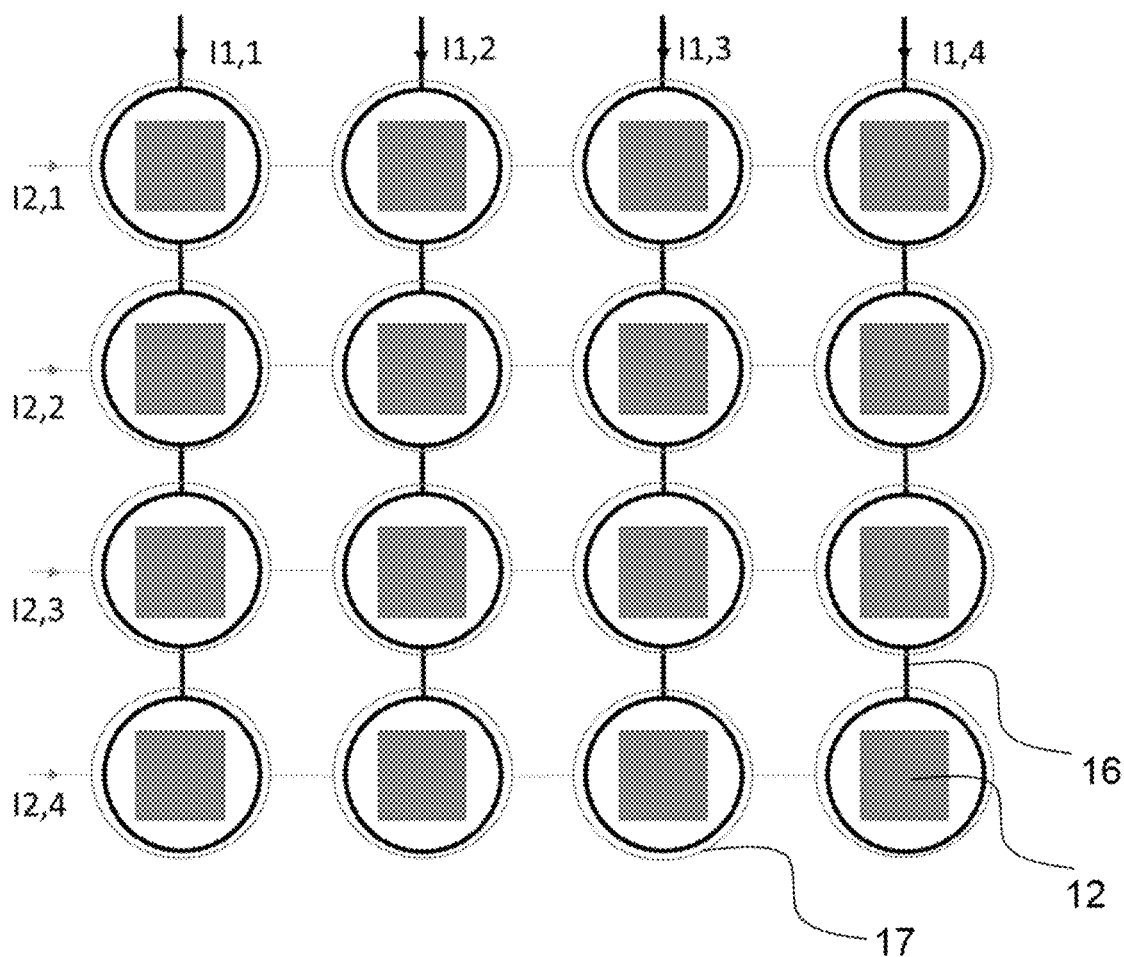
FIG. 8 shows nanoparticle samples presented in multiple excitation groups at the same time.

In an embodiment shown in FIG. 8, instead of feeding the individual coils around each nanoparticle sample (12) separately, coils (16) are fed in groups (17). A nanoparticle sample (12) is present in multiple groups (17) at the same time. By setting the applied current in each group (17), each nanoparticle sample (12) can be electronically shifted to the desired position. Thus, the required number of feed lines is reduced.

In order for the electronic calibration method to operate correctly, the magnetic field generated by the MPI system must not be altered by the presence of the electronic calibration scene. In addition, the magnetic field that the coils (15a, 15b, 15c) around the exemplary nanoparticles (12) surround should not be affected by the secondary magnetic field. For this purpose, the coils (15a, 15b, 15c) must be driven by a constant current source, in which the secondary magnetic field frequency of the MPI system is filtered out.

The whole nanoparticle sample (12) should be exposed to the same magnetic field amplitude. To this end, the coil structure around the nanoparticle sample (12) may consist of two or more separate coils parallel to each other as in a Helmholtz coil (18) configuration. The Helmholtz coil structure uses two coils whose radii are equal to the distance between them. With this configuration, maximum magnetic field homogeneity is obtained.

Figure 9:
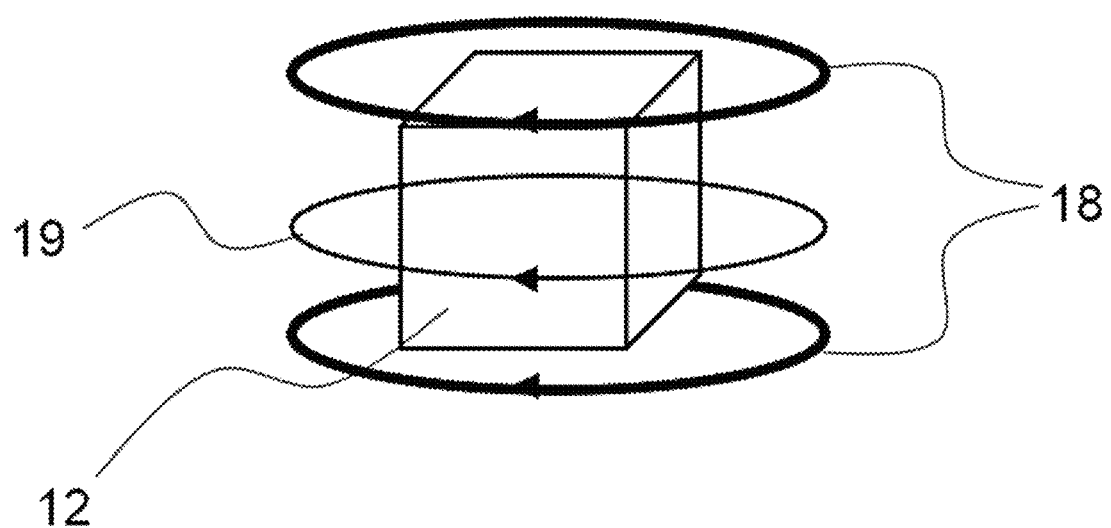
FIG. 9 shows a nanoparticle sample with a Helmholtz coil for applying an axial magnetic field and a receiver coil for measuring the applied magnetic field.

The dependence of the magnetic field generated by the coils (15a, 15b, 15c) on the applied current must be known. This can be achieved using receiver coils that measure the magnetic field around each nanoparticle sample (12). Thus, the applied magnetic field can be continuously monitored. FIG. 9 shows an embodiment with a Helmholtz coil (18) for applying an axial magnetic field to the nanoparticle sample (12), and a receiver coil (19) for measuring the applied magnetic field.

Figure 10:
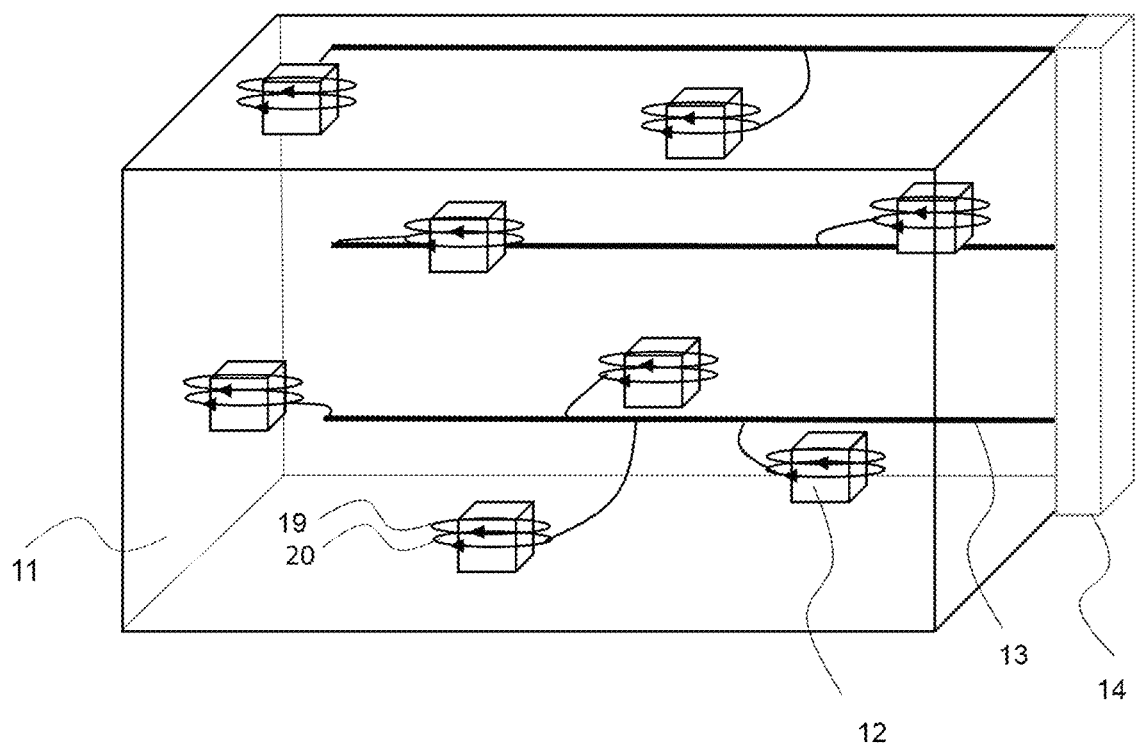
FIG. 10 shows a calibration scene comprising a transmitter and a receiver coil for each nanoparticle sample.

Since the amount of displacement of the nanoparticle samples (12) with respect to the applied magnetic field is also dependent on the magnetic field gradient of the MPI system, the magnetic field gradient at each position must be known. The magnetic field gradient at each voxel can be measured by scanning a magnetic field probe before electronic calibration. However, this measurement would take a long time. The gradient field can also be determined by measuring the magnetic field using the receiving coils (19) around the nanoparticle samples (12). A calibration scene comprising a transmitter coil (20) and a receiver coil (19) is shown in FIG. 10. In the case where the transmitter coils (20) are inactive, the magnetic field gradient of the MPI system is measured using magnetic field measurements from receiver coils (19) around all of the nanoparticle samples (12). In an alternative embodiment, the transmitting coils (20) may be used for measuring the magnetic field of the MPI system, eliminating the need for a separate receiver coil (19).

REFERENCES

[1] Weizenecker J, Gleich B, Rahmer J, Dahnke H, Borgert J (2009). Three-dimensional real-time in vivo magnetic particle imaging, Phys Med Biol. 2009; 54: L1-L10.
[2] A. v. Gladiss, M. Graeser, P. Szwargulski, T. Knopp and T. M. Buzug. Hybrid system calibration for multidimensional magnetic particle imaging. Phys. Med. Biol., vol. 62, no. 9, pp. 3392, 2017.
[3] Compressed Sensing Theory and Applications, Ed. By Y. C. Eldar, G. Kutyniok, Cambridge University Press, New York, 2012.
[4] B. Gleich and J. Weizenecker. Tomographic imaging using the nonlinear response of magnetic particles. Nature, 435(7046):1217-1217, 2005. doi: 10.1038/nature03808.
[5] T. Knopp, J. Rahmer, T. F. Sattel, S. Biederer, J. Weizenecker, B. Gleich, J. Borgert, and T. M. Buzug. Weighted iterative reconstruction for magnetic particle imaging. Phys. Med. Biol., vol. 55, no. 6, pp. 1577-1589, 2010. doi:10.1088/0031-9155/55/6/003.
[6] G. R. Arce, D. J. Brady, L. Carin, H. Arguello, and D. S. Kittle, "Compressive Coded Aperture Spectral Imaging," IEEE Signal Processing Magazine, vol. 31, no. 1, pp. 105-115, 2014.
[7] S. Ilbey et al., "Comparison of system-matrix-based and projection-based reconstructions for field free line magnetic particle imaging," International Journal on Magnetic Particle Imaging, vol. 3, no. 1, 2017.
[8] H. E Güven, A. Güngör, and M. Cetin, "An Augmented Lagrangian Method for Complex-Valued Compressed SAR Imaging," IEEE Trans. Comput. Imaging, 2(3):235-250, 2016.

What is claimed is:

1. An electronic calibration method for a magnetic particle imaging (MPI) system that comprises a measurement device, comprising the steps of:
   placing a plurality of nanoparticle samples inside a calibration scene,
   surrounding each of the plurality of nanoparticle samples with one or more electromagnets per nanoparticle sample,
   applying a current to the one or more electromagnets, of two or more of the plurality of nanoparticle samples at a same time, to cause a magnetic field offset at a desired amplitude to virtually move the plurality of nanoparticle samples to a desired position, the current being applied using an interface to a plurality of grouped feed lines, each feed line, of the plurality of grouped feed lines, applying current to separate groups of separate coils around each of two or more nanoparticle samples of the plurality of nanoparticle samples, the feed lines distributed across the calibration scene, wherein the plurality of nanoparticle samples are randomly or pseudo-randomly distributed in the calibration scene,
   generating a system matrix with compressed sensing methods by using measurements taken for different current excitations of the one or more electromagnets, the different current excitations being generated at a same time, wherein the plurality of nanoparticles samples are virtually in different positions,
   wherein the one or more electromagnets is at least one coil,
   where a structure of the coils around each of the two or more nanoparticle samples of the plurality of nanoparticle samples consists of two or more separate coils parallel to each other as in a Helmholtz coil configuration to obtain a maximum magnetic field homogeneity on each nanoparticle sample.

2. The electronic calibration method according to claim 1, comprising the step of reconstructing the system matrix by using the following inequality:

$$\underset{A}{\operatorname{argmin}} \|DA^T\|_1 \text{ subject to } \|(PD^T)DA^T - A_p\|_2 < \varepsilon_p,$$

wherein P is a nanoparticle density distribution in a field of view at each measurement position, D is a transformation matrix for transforming A into a sparse domain, A is the system matrix, $A_p$ is a measurement matrix converted to a Fourier space for the each measurement position of a coded calibration scene, $\varepsilon_p$ represents a constant related to an error caused by a system noise.

3. The electronic calibration method according to claim 1, wherein the calibration scene is larger than or equal to a field of view of the MPI system.

4. The electronic calibration method according to claim 1, wherein each of the plurality of nanoparticle samples are surrounded by the one or more electromagnets in two different axes to create a virtual movement in the two different axes.

5. The electronic calibration method according to claim 1, wherein each of the plurality of nanoparticle samples are surrounded by the one or more electromagnets in three different axes to create a virtual movement in the three different axes.

6. The electronic calibration method according to claim 1, wherein a number of the plurality of nanoparticle samples is less than 20% of a total number of voxels where the plurality of nanoparticles samples are placed.

7. The electronic calibration method according to claim 1, wherein the one or more electromagnets are fed separately or in groups.

8. An electronical calibration apparatus for a magnetic particle imaging (MPI) system, comprising;
   a calibration scene with distributed nanoparticle samples inside a volume of the calibration scene, wherein the calibration scene is larger than or equal to a field of view of the MPI system, wherein the distributed nanoparticle samples are randomly or pseudo-randomly distributed in the calibration scene;
   at least one electromagnet around each nanoparticle of the distributed nanoparticle samples, the system having at least one electromagnet per nanoparticle sample;
   an electronical interface for connection to the MPI system configured to excite the at least one electromagnet around each nanoparticle of the distributed nanoparticle samples at a same time, and to receive a signal from the at least one electromagnet; and
   a plurality of grouped feed lines from the electronical interface, each feed line, of the plurality of grouped feed lines, configured to apply current to separate groups of separate coils around each of two or more nanoparticle samples of the plurality of nanoparticle samples, the feed lines distributed across the calibration scene,
   wherein the at least one electromagnet is a coil, and
   wherein a structure of the coil around each of the two or more nanoparticle samples of the plurality of nanoparticle samples consists of two or more separate coils parallel to each other as in a Helmholtz coil configuration to obtain a maximum magnetic field homogeneity on each nanoparticle sample.

9. The electronical calibration apparatus according to claim 8, further comprising at least one receiver coil for monitoring a magnetic field and a gradient field around each nanoparticle sample.

10. The electronical calibration apparatus according to claim 8, wherein coils used for transmitting are used for measuring a magnetic field of the MPI system.

11. The electronical calibration apparatus according to claim 8, wherein the coils are driven by a constant current source, in which a secondary magnetic field frequency of the MPI system is filtered out.

* * * * *